(12) United States Patent
Bardenstein et al.

(10) Patent No.: US 7,819,527 B2
(45) Date of Patent: Oct. 26, 2010

(54) APPARATUS AND METHOD FOR ASSESSING EYE DISEASE

(75) Inventors: David S. Bardenstein, Shaker Heights, OH (US); Dennis Patfield, Willowick, OH (US)

(73) Assignee: Case Western Reserve University, Cleveland, OH (US)

( * ) Notice: Subject to any disclaimer, the term of this patent is extended or adjusted under 35 U.S.C. 154(b) by 185 days.

(21) Appl. No.: 12/101,359

(22) Filed: Apr. 11, 2008

(65) Prior Publication Data

US 2009/0021698 A1    Jan. 22, 2009

Related U.S. Application Data

(60) Provisional application No. 60/911,597, filed on Apr. 13, 2007.

(51) Int. Cl.
*A61B 3/02* (2006.01)
(52) U.S. Cl. ..................................................... 351/225
(58) Field of Classification Search .................. 351/225
See application file for complete search history.

(56) References Cited

U.S. PATENT DOCUMENTS

| 2,643,458 | A | | 6/1953 | Kellems |
| 5,302,981 | A | | 4/1994 | Wirtz |
| 5,392,525 | A | | 2/1995 | Chow |
| 5,506,631 | A | * | 4/1996 | Boothe et al. ............... 351/200 |
| 5,950,320 | A | | 9/1999 | Dorsey |
| 2006/0227289 | A1 | | 10/2006 | Hasegawa |

* cited by examiner

*Primary Examiner*—Joseph Martinez
(74) *Attorney, Agent, or Firm*—Tarolli, Sundheim, Covell & Tummino LLP

(57) ABSTRACT

An apparatus for assessing eye disease in a subject includes a body member including an arm portion, a handle portion, and an alignment portion. The arm and handle portions each have a first end portion oppositely disposed from a second end portion. Each of the first end portions are operably connected to the alignment portion. The arm portion includes a scale in degrees, and the alignment portion includes an alignment mechanism for aligning the body member with the visual field of the subject.

18 Claims, 10 Drawing Sheets

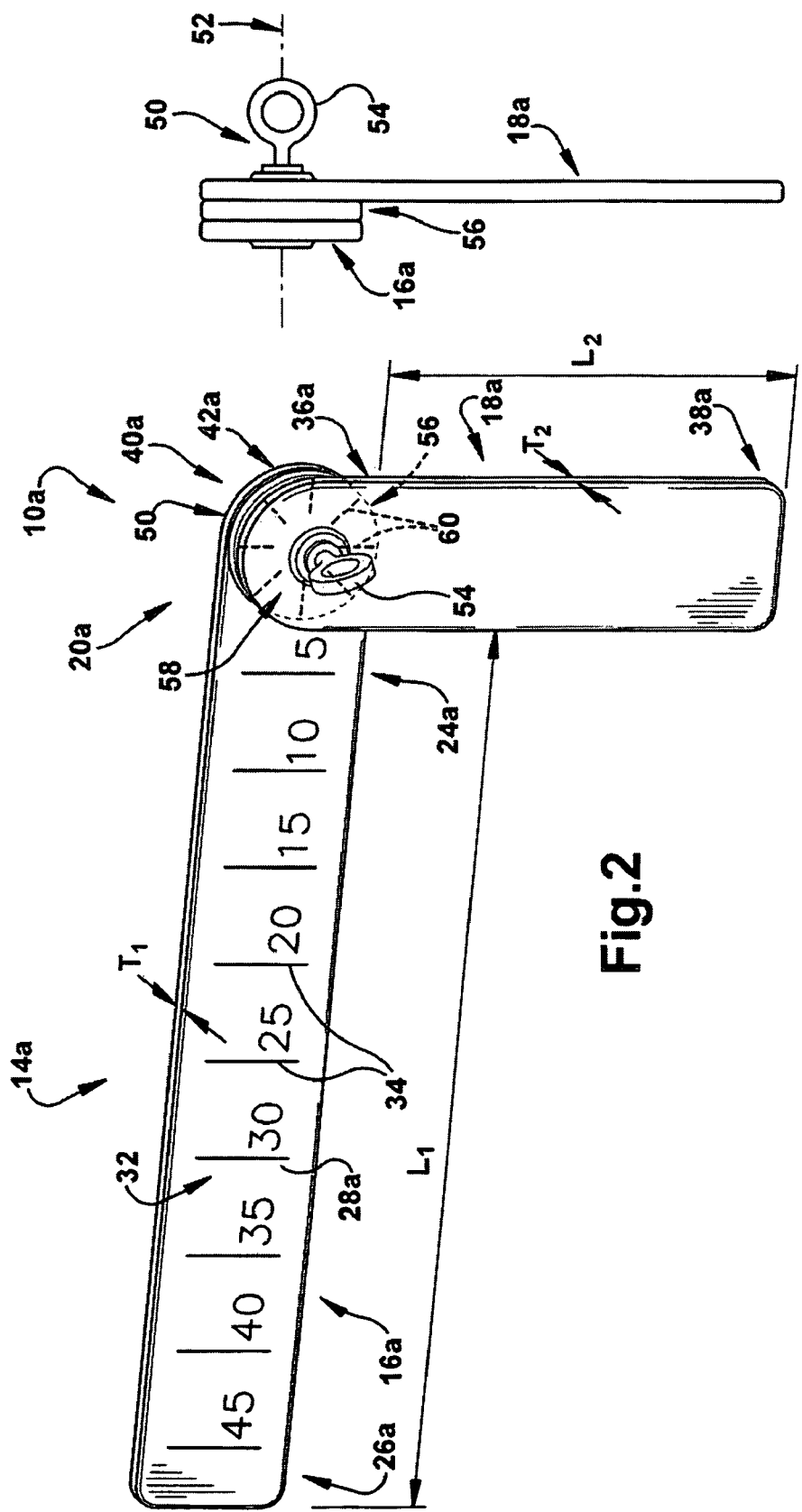

APPARATUS AND METHOD FOR ASSESSING EYE DISEASE

RELATED APPLICATION

This application claims priority from U.S. Provisional Application No. 60/911,597, filed Apr. 13, 2007, the subject matter, which is incorporated herein by reference.

TECHNICAL FIELD

The present invention generally relates to an apparatus and method for assessing eye disease, and more particularly to an apparatus and method for assessing diplopia and nystagmus.

BACKGROUND OF THE INVENTION

The assessment of single and double vision (diplopia) are important in a variety of conditions which affect the alignment of the eyes and extraocular muscle function. This information can be used to detect and quantitate the degree of double vision, for example, and thus has both diagnostic and therapeutic applications.

Current methods for assessing double vision involve the use of devices originally developed to assess conditions other than double vision. One group of tests includes the tangent and Hess screen tests. These tests use a flat test area without a means for verifying eye position at the time double vision is reported. Another related test, known as the Goldmann test, uses a visual field testing device with test lights disposed in a large white bowl.

Other approaches currently used to estimate diplopia involve measuring displacement of corneal light relative to known landmarks in the front of the eye. Such tests provide only minimal quantitative information and can vary significantly based on measurements obtained by different examiners. More recently, equipment for detecting head alignment in patients with spinal cord disorders has been adapted to estimate diplopia. These methods offers precise quantification but include significant shortcomings such as high cost, large and unwieldy equipment, and an availability, which is typically limited to only subspecialists.

One significant drawback to existing methods for assessing diplopia is that eye position cannot be correlated to a patient's report of double vision. This is important since the brain can suppress input from one eye in order to avoid diplopia. Additionally, significant deviations of the eye muscles can be missed without viewing the patient's eyes from the front during examination. A need therefore exists for a simple, accurate, and quantitative means for assessing eye diseases.

SUMMARY OF THE INVENTION

In one aspect of the present invention, an apparatus for assessing eye disease in a subject comprises a body member having an arm portion, a handle portion, and an alignment portion. The arm and handle portions each have a first end portion oppositely disposed from a second end portion. Each of the first end portions are operably connected to the alignment portion. The arm portion includes a scale in degrees, and the alignment portion includes an alignment mechanism for aligning the body member with the visual field of the subject.

In another aspect of the present invention, a method for assessing diplopia is provided. One step of the method includes providing a body member having an arm portion, a handle portion, and an alignment portion. The arm and handle portions each have a first end portion oppositely disposed from a second end portion. Each of the first end portions is operably connected to the alignment portion. The arm portion includes a scale in degrees, and the alignment portion includes an alignment mechanism for aligning the body member with the visual field of the subject. The alignment mechanism of the alignment portion is aligned with the visual field of the subject. Next, a target is moved radially outward from the alignment portion towards the arm portion. The point on the scale where diplopia occurs is then determined.

In another aspect of the present invention, a method for assessing nystagmus is provided. One step of the method includes providing a body member having an arm portion, a handle portion, and an alignment portion. The arm and handle portions each have a first end portion oppositely disposed from a second end portion. Each of the first end portions is operably connected to the alignment portion. The arm portion includes a scale in degrees, and the alignment portion includes an alignment mechanism for aligning the body member with the visual field of the subject. The alignment mechanism of the alignment portion is aligned with the visual field of the subject. Next, a target is moved radially outward from the alignment portion towards the arm portion. The point on the scale where nystagmus occurs is then determined.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2 is a perspective view showing an alternative embodiment of the apparatus in FIG. 1;

FIG. 3 is a cross-sectional view taken along Line A-A in FIG. 2;

DETAILED DESCRIPTION

Figure 1:
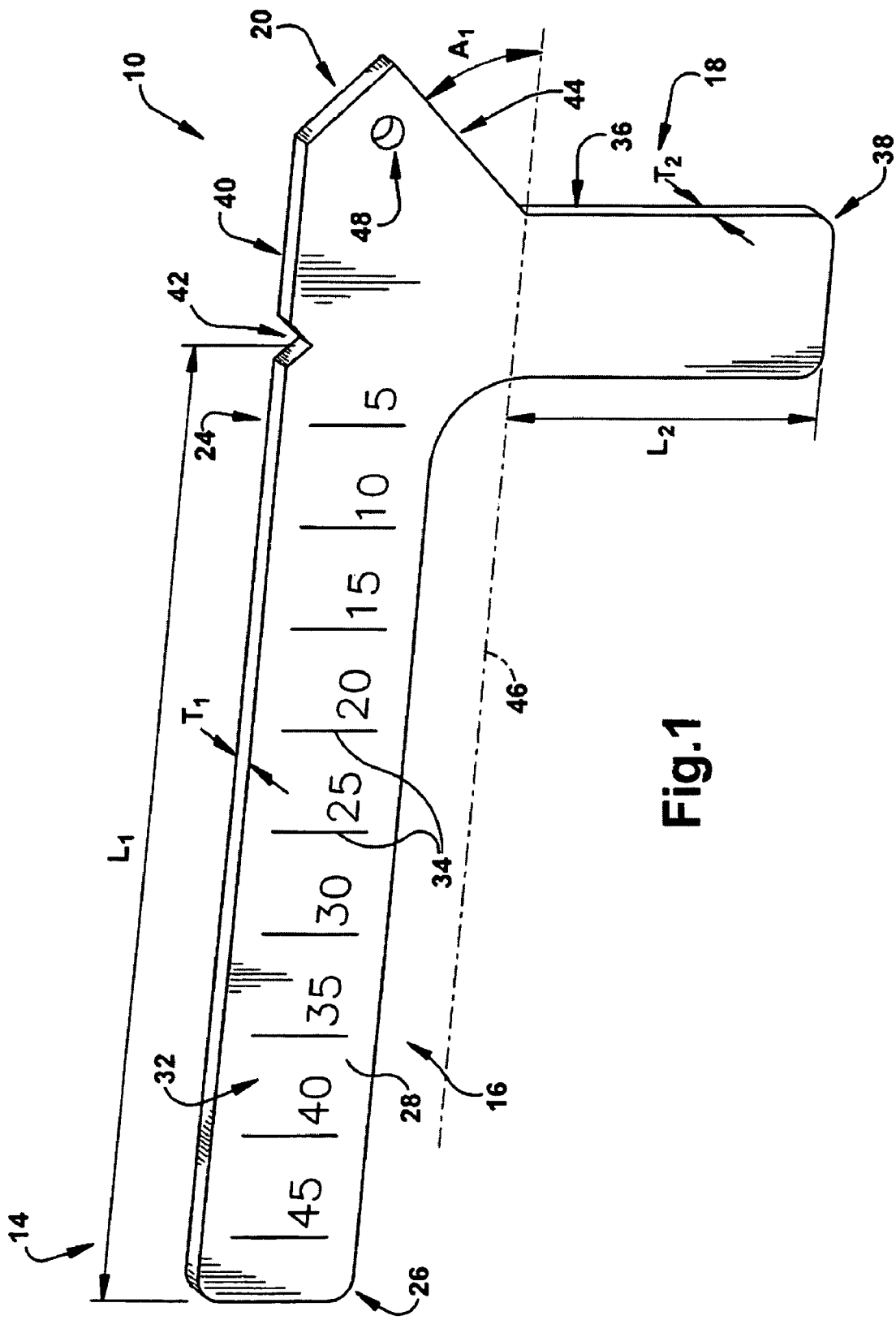
FIG. 1 is a perspective view showing an apparatus for assessing eye disease constructed in accordance with the present invention.

The present invention generally relates to an apparatus and method for assessing eye disease, and more particularly to an apparatus and method for assessing diplopia and nystagmus. As representative of the present invention, FIGS. 1-2 illustrate an apparatus 10 for assessing eye disease in a subject 12 (FIG. 11) comprising a body member 14 (FIG. 1) having an arm portion 16 and a handle portion 18 operably connected to an alignment portion 20.

Unless otherwise defined, all technical terms used herein have the same meaning as commonly understood by one of ordinary skill in the art to which the present invention pertains.

In the context of the present invention, the term "eye disease" refers to any variety of diseases, impairments, or defects that cause vision loss, blurred or decreased close-up and distance vision, blind spots, objects to appear a different color or shape, neuro-ophthalmic manifestations of vascular eye diseases, including ischemic optic neuropathy, anterior ischemic optic neuropathy, retinal artery occlusion, asymptomatic retinal emboli, asymptomatic retinal embolus or ischemia of retinal tissue, retinal edema, amaurosis fugax, reduction in visual field, occlusion of ocular vessels, stagnation of blood flow within the arteriole, cataracts, glaucoma, proptosis, eyelid retraction, restrictive myopathy, diplopia, nystagmus, compressive optic neuropathy, and/or exposure keratopathy. It is not intended that the present invention be limited to treating any particular underlying disease resulting in vision defects or impairments.

As used herein, the term "diplopia" refers to the perception of two images from a single object generally caused by incorrect alignment of the eyes while focused on the object. The images may be horizontal, vertical, or diagonal. The term can include both binocular and monocular diplopia. Binocular diplopia can occur when the two eyes are not correctly aligned while aiming at an object. When the eyes are misaligned and aimed at different targets, two non-matching images are sent to the brain. When the brain accepts and uses two non-matching images simultaneously, double vision results. Diplopia can also occur when viewing with only one eye; this is called monocular diplopia, or where the patient perceives more than two images, monocular polyopia. In this case, the multiple vision can be caused by a structural defect in the vision system, such as cataracts, subluxation of the crystalline lens or Keratoconus causing irregularities in the refraction of light within the eye.

As used herein, the term "nystagmus" refers to involuntary eye movement that can be part of the vestibulo-ocular reflex, with the eyes moving first in the direction of the lesioned side (slow phase) followed by a quick correction (fast phase) to the opposite side or away from the lesioned side. The direction of nystagmus is defined by the direction of its quick phase (e.g., a right-beating nystagmus is characterized by a rightward-moving quick phase). The oscillations may occur in the vertical, horizontal or torsional planes, or in any combination. The resulting nystagmus is often named as a gross description of the movement, e.g., downbeat nystagmus, upbeat nystagmus, seesaw nystagmus, and periodic alternating nystagmus.

As used herein, the term "visual field" refers to the total area in which objects can be seen in the peripheral vision while the eye is focused on a central point.

As used herein, the term "subject" refers to any warm-blooded animal, preferably mammals, including humans.

To address the problems associated with eye disease, and more particularly diplopia and nystagmus, the present invention provides an apparatus 10 and method 22 (FIGS. 10 and 16) for assessing eye alignment and extraocular muscle function. More particularly, the present invention provides a simple apparatus 10 (FIG. 1) that permits quick and accurate assessment of diplopia and nystagmus by professional and non-professional eye care providers.

One embodiment of the present invention is illustrated in FIG. 1. As shown in FIG. 1, an apparatus 10 for assessing eye disease comprises a body member 14 having an arm portion 16 and a handle portion 18 operably connected to an alignment portion 20. The body member 14 is made of a rigid, transparent material such as hardened plastic, silicon, polyurethane, or the like. It will be appreciated, however, that the entire body member 14 need not be transparent. For example, only select portions of the body member 14, such as the arm and handle portions 16 and 18, may be transparent.

Figure 4:
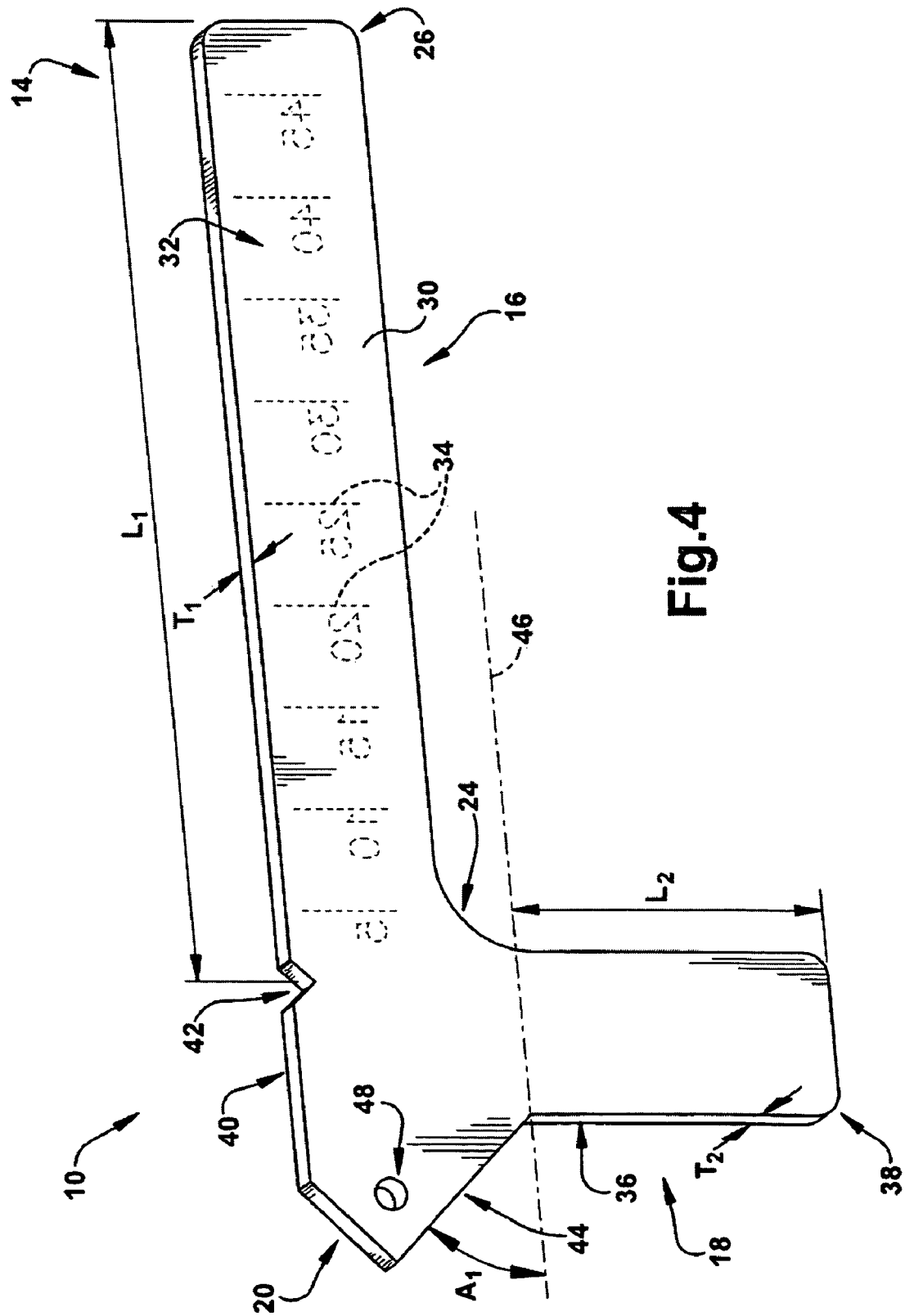
FIG. 4 is a perspective view showing a second side of the apparatus in FIG. 1.

The arm portion 16 of the body member 14 has a generally elongated, rectangular shape defined by a thickness $T_1$ and a length $L_1$. The arm portion 16 includes a first end portion 24 oppositely disposed from a second end portion 26 and oppositely disposed first and second sides 28 and 30 (FIG. 4). The thickness $T_1$ of the arm portion 16 (FIG. 1) can include any desired width. For example, the thickness may be about 0.125 inches to about 0.5 inches wide. The length $L_1$ of the arm portion 16 can include any desired length. For example, the length $L_1$ may be about 8 to about 20 inches, and more preferably about 16 inches. A desired length $L_1$ is determined by calibrating the apparatus 10, which is described in detail below.

As shown in FIG. 1, the arm portion 16 also includes a scale 32 located on the first side 28 of the body member 14. The scale 32 comprises a plurality of indices 34 spaced along the first side 28 of the arm portion 16. The scale 32 is measured in degrees, with each of the indices 34 indicating a pre-calibrated value (in degrees). Placement of the indices 34 on the arm portion 16 and the respective degree values associated with each of the indices is determined by calibrating the apparatus 10 (described below). The scale 32 shown in FIG. 1 includes nine indices 34. A first indices 34 of 5° is located near the first end portion 24 of the arm portion 16 and additional indices are progressively located along the first side 28 of the arm portion. As described in more detail below, the scale 32 can be used to indicate eye alignment and extraocular muscle function.

It will be appreciated that the scale 32 may be located on the first side 28 of the arm portion 16 as shown in FIG. 1 or, alternatively, on both the first and second sides 30 (not shown). Additionally, it will be appreciated that the scale 32 may include a greater or less number of indices 34 than are shown in FIG. 1. For example, the scale 32 may include additional indices 34 to indicate single degree increments, i.e., in addition to the 5° increments shown in FIG. 1. Further, it should be appreciated that the scale 32 may include a range of degrees greater or less than the range shown in FIG. 1. For example, the scale 32 may include a range of degrees from 0° to 90°.

The body member 14 also includes a handle portion 18 for holding and adjusting the position of the body member. The handle portion 18 includes a first end portion 36 oppositely disposed from a second end portion 38. The handle portion 18 is defined by a thickness $T_2$ and a length $L_2$. The thickness $T_2$ and length $L_2$ can be any appropriate dimension that facilitates use of the body member 14. For example, the thickness $T_2$ of the handle portion 18 can be about 0.25 inches to about 0.5 inches. The length $L_2$ of the handle portion 18 can be any length suitable to facilitate use of the body member 10, such as about 3 inches to about 6 inches, for example. The handle portion 18 may include a gripping device or pad (not shown), such as padded tape or foam attached to a portion of the handle portion, for improving handling and comfort characteristics of the body member 14.

Figure 5:
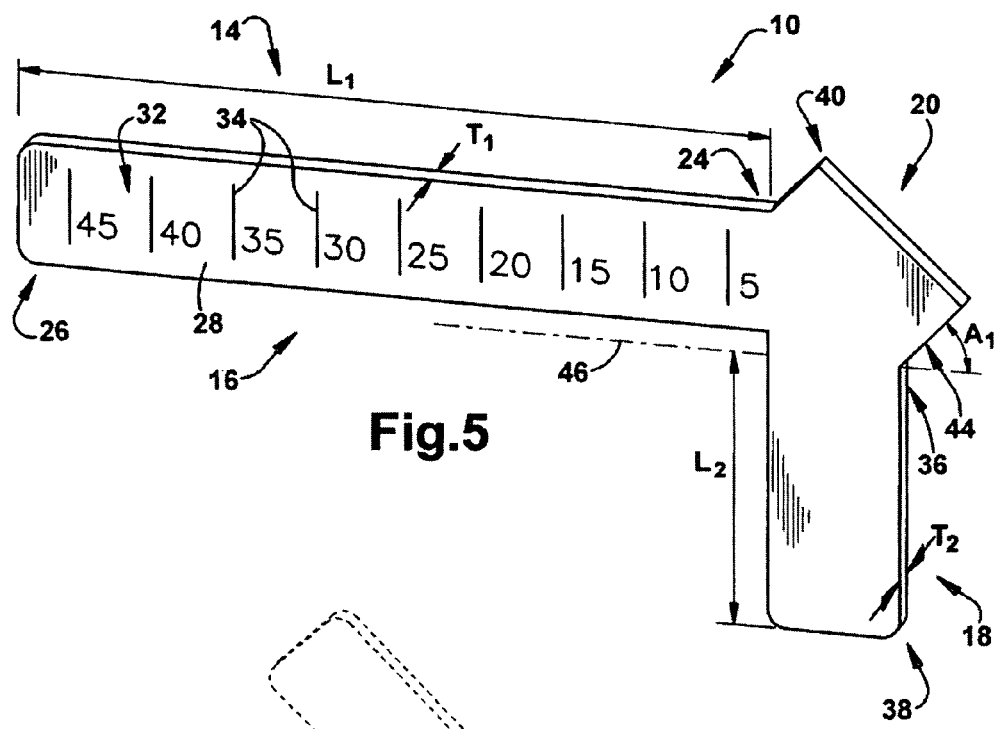
FIG. 5 is a perspective view showing another alternative embodiment of the apparatus in FIG. 1.

The first end portion 24 of the arm portion 16 and the first end portion 36 of the handle portion 18 are each fixed to the alignment portion 20 such that the body member 14 has a rigid, L-shaped configuration. The alignment portion 20 may have a variety of shapes and configurations, such as those shown in FIGS. 1 and 5. The alignment portion 20 includes an alignment mechanism 40 for aligning the body member 14 with the visual field of the subject 12.

The alignment mechanism 40 includes an indicator 42 for aligning the alignment portion 20 of the body member 14 with an index point on the subject 12, such as the bridge of the subject's nose. As shown in FIG. 1, the indicator 42 includes a V-shaped notch located at the first end portion 24 of the arm portion 16. The indicator 42 may have any other suitable shape or configuration, such as a U-shaped configuration, for example. Additionally or optionally, the indicator 42 may include some other clearly visible configuration, such as semi-transparent or colored markings (e.g., a line or series of lines) (not shown) to facilitate alignment of the alignment portion 20 with the index point on the subject 12.

Figure 6:
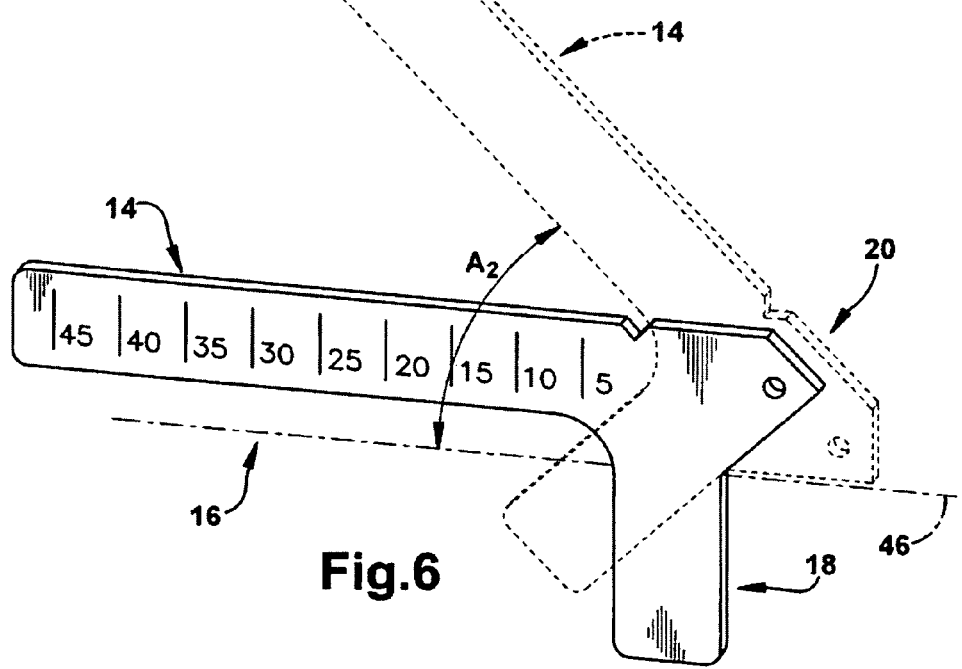
FIG. 6 is a perspective view showing the apparatus of FIG. 1 in a first position (solid line) and second position (dashed line)
Figure 7:
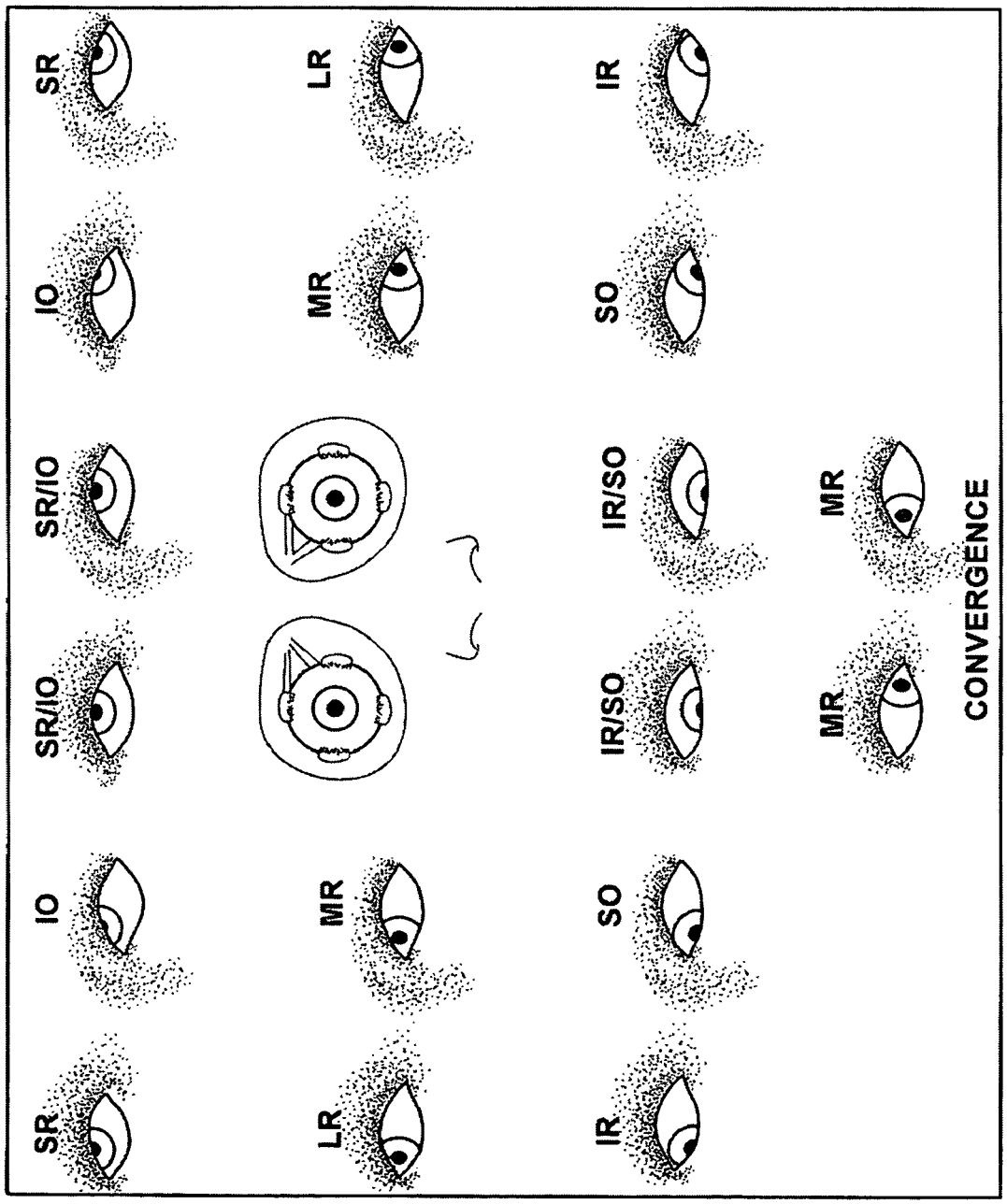
FIG. 7 is an illustration showing the six cardinal gaze positions as well as the upward and downward gaze positions.

The alignment mechanism 40 also includes a reference surface 44 for adjusting the position of the body member 14, and more particularly the position of the arm portion 16. The reference surface 44 has an angled, linear shape and forms a first angle $A_1$ with respect to a reference point 46 (e.g., the ground). As shown in FIG. 1, the first angle $A_1$ is about 45° when the arm portion 16 is positioned parallel to the reference point 46. As described in more detail below, the position of the body member 14 may be adjusted such that the first angle $A_1$ is equal to about 0° and a second angle $A_2$ of about 45° is formed between the reference point 46 and the arm portion 16 (FIG. 6). The reference surface 44 permits quick and accurate movement of the arm portion 16 into any one of the six cardinal gaze positions, as well as the upward and downward gaze positions (FIG. 7).

The alignment portion 20 also comprises at least one storage mechanism 48 so that the body member 14 can be easily stored when not in use. As shown in FIG. 1, the storage mechanism 48 comprises a circular opening extending through the alignment portion 20. When the body member 14 is not in use, the body member may be hung on a wall, for example, by placing a hook (e.g., mounted to a wall) through the circular opening. It will be appreciated that the storage mechanism 48 may comprise other suitable shapes and/or devices, such as a hook (not shown) or flexible material formed into a loop (not shown) and securely attached to the body member 14 to store the body member when not in use.

Another embodiment of the present invention is illustrated in FIG. 2. In FIG. 2, an apparatus $10_a$ for assessing eye disease is provided. The apparatus $10_a$ is identical to the apparatus 10 illustrated in FIG. 1, except where as described below. In FIG. 2, structures that are identical as structures in FIG. 1 use the same reference numbers, whereas structures that are similar but not identical carry the suffix "a".

As shown in FIG. 2, the apparatus $10_a$ comprises a body member $14_a$ having an arm portion $16_a$ and a handle portion $18_a$ operably connected to an alignment portion $20_a$. The body member $14_a$ is made of a rigid, transparent material such as hardened plastic, silicon, polyurethane, or the like. It will be appreciated, however, that the entire body member $14_a$ need not be transparent. For example, only select portions of the body member $14_a$, such as the arm and handle portions $16_a$ and $18_a$, may be transparent.

Figure 8:
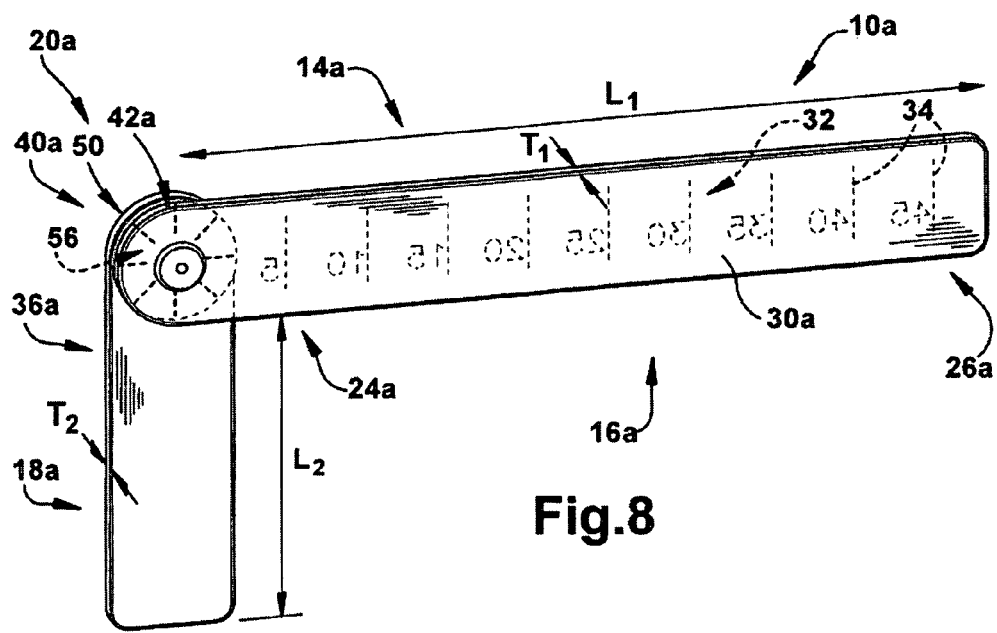
FIG. 8 is a perspective view of an alternative embodiment of the apparatus in FIG. 1.

The arm portion $16_a$ of the body member $14_a$ has a generally elongated, rectangular shape defined by a thickness $T_1$ and a length $L_1$. The arm portion $16_a$ includes a first end portion $24_a$ oppositely disposed from a second end portion $26_a$ and oppositely disposed first and second sides $28_a$ and $30_a$ (FIG. 8). The thickness $T_1$ of the arm portion (FIG. 2) can include any desired width. For example, the thickness may be about 0.125 inches to about 0.5 inches wide. The length $L_1$ of the arm portion $16_a$ can include any desired length. For example, the length $L_1$ may be about 8 to about 20 inches, and more preferably about 16 inches. A desired length $L_1$ is determined by calibrating the body member $14_a$ (as described below).

As shown in FIG. 2, the arm portion $16_a$ also includes a scale 32 on the first side $28_a$ of the body member $14_a$. The scale 32 comprises a plurality of indices 34 spaced along the first side $28_a$ of the arm portion $16_a$. The scale 32 is measured in degrees, with each of the indices 34 indicating a pre-calibrated value (in degrees). Placement of the indices 34 on the arm portion $16_a$ and the respective degree values is determined by calibrating the body member $14_a$ as described above. The scale 32 shown in FIG. 2 includes nine indices 34. A first indices 34 of 5° is located near the first end portion $24_a$ of the arm portion $16_a$ and additional indices are progressively located along the first side $28_a$ of the arm portion. As described in more detail below, the scale 32 can be used to indicate eye alignment and extraocular muscle function.

It will be appreciated that the scale 32 may be located on the first side $28_a$ of the arm portion $16_a$ as shown in FIG. 2 or, alternatively, on both the first side and the second side $30_a$ (not shown). Additionally, it will be appreciated that the scale 32 may include a greater or lesser number of indices 34 than are shown in FIG. 2. For example, the scale 32 may include additional indices 34 to indicate single degree increments, i.e., in addition to 5° increments as shown in FIG. 2. Further, it should be appreciated that the scale 32 may include a range of degrees greater or less than the range shown in FIG. 1. For example, the scale 32 may include a range of degrees from 0° to 90°.

The body member $14_a$ also includes a handle portion $18_a$ for holding and adjusting the position of the body member. The handle portion $18_a$ includes a first end portion $36_a$ oppositely disposed from a second end portion $38_a$. The handle portion $18_a$ is defined by a thickness $T_2$ and a length $L_2$. The thickness $T_2$ and length $L_2$ can be any appropriate dimension that facilitates use of the body member 14. For example, the thickness $T_2$ of the handle portion $18_a$ can be about 0.25 inches to about 0.5 inches. The length $L_2$ of the handle portion $18_a$ can be any length suitable to facilitate use of the body member $14_a$, such as about 3 inches to about 6 inches, for example. The handle portion $18_a$ may include a gripping device or pad (not shown), such as padded tape or foam attached to a portion of the handle portion, for improving handling and comfort characteristics of the body member $14_a$.

The first end portion $24_a$ of the arm portion $16_a$ and the first end portion $36_a$ of the handle portion $18_a$ are each operably connected to the alignment portion $20_a$ via a hinge mechanism 50 such that the arm and handle portions are freely rotatable about a radial axis 52. As shown in FIGS. 2-3, the hinge mechanism 50 comprises a screw 54 or pin extending through each of the handle portion $18_a$, a reference wheel 56, and the arm portion $16_a$. The screw 54 can be adjusted (i.e., tightened or loosened) to selectively adjust the position of the arm portion $16_a$. For example, the screw 54 may first be loosened and the arm portion $16_a$ adjusted so that the arm portion is parallel to a reference point 46. The screw 54 may then be tightened to secure the arm portion $16_a$ and provide a rigid, L-shaped body member $14_a$ (FIG. 2). Alternatively, the screw 54 may be loosened again and the arm portion $16_a$ rotated about the radial axis 52 so that the arm portion forms a third angle $A_3$. The screw 54 may then be tightened to secure the arm portion $16_a$ at the third angle $A_3$.

The alignment portion $20_a$ of the body member $14_a$ includes an alignment mechanism $40_a$ for aligning the body member with the visual field of the subject 12. The alignment mechanism $40_a$ includes an indicator $42_a$ for aligning the alignment portion $20_a$ with an index point of the subject 12, such as the bridge of the subject's nose. As shown in FIG. 2, the indicator $42_a$ comprises the screw 54. It will be appreciated, however, that the indicator $42_a$ can include a notch (e.g., similar or identical to the one illustrated in FIG. 1) (not shown) or any other clearly visible marking capable of facilitating alignment of the alignment portion $20_a$ with the index point on the subject 12.

The alignment mechanism $40_a$ also includes a reference wheel 56 for adjusting the position of the body member $14_a$, and in particular the position of the arm portion $16_a$. As shown in FIG. 3, the reference wheel 56 is disposed between the arm portion $16_a$ and the handle portion $18_a$. The reference 56 wheel includes a scale 58 in degrees and a plurality of indices 60. Each of the indices 60 corresponds to a pre-determined value (in degrees). As shown in FIG. 2, for example, there are eight indices 60 located on the reference wheel 56. As described below, the number and placement of the indices 60 is determined by calibrating the body member $14_a$.

Figure 9:
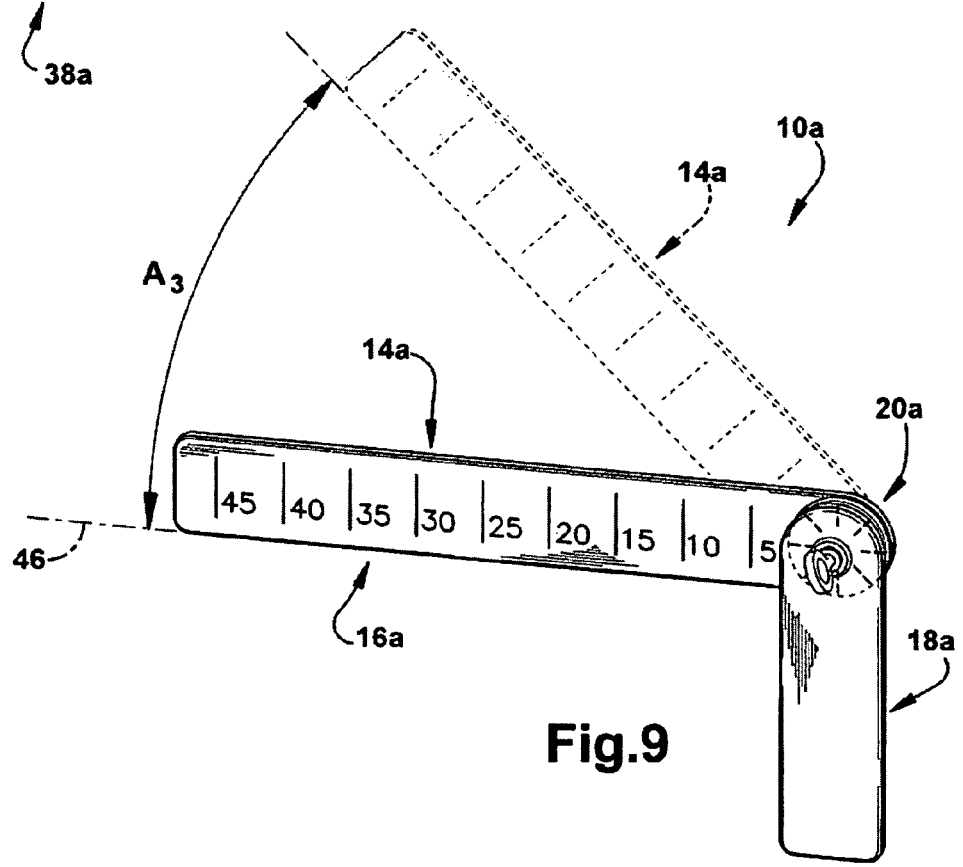
FIG. 9 is a perspective view showing the apparatus in FIG. 8 in a first position (solid line) and a second position (dashed line)

The reference wheel 56 is used to adjust the position of the arm portion $16_a$. As shown in FIG. 9, for example, the arm portion $16_a$ is rotated so that the arm portion is aligned with a particular indices 60. By aligning the arm portion $16_a$ with a particular indices 60 located on the reference wheel 56, the arm portion may be rotated to form a desired third angle $A_3$.

Although not shown in FIG. 2, it will be appreciated that the body member $14_a$ may also include at least one storage mechanism (not shown) for storing the body member $14_a$ when not in use. For example, a circular opening similar to the one shown in FIG. 1 may be located on the handle portion $18_a$ of the body member $14_a$. It will be appreciated that the storage mechanism may comprise any other suitable shape and/or device, such as a hook (not shown) or flexible material formed into a loop (not shown) and securely attached to the body member $14_a$ to store the body member when not in use.

Figure 10:
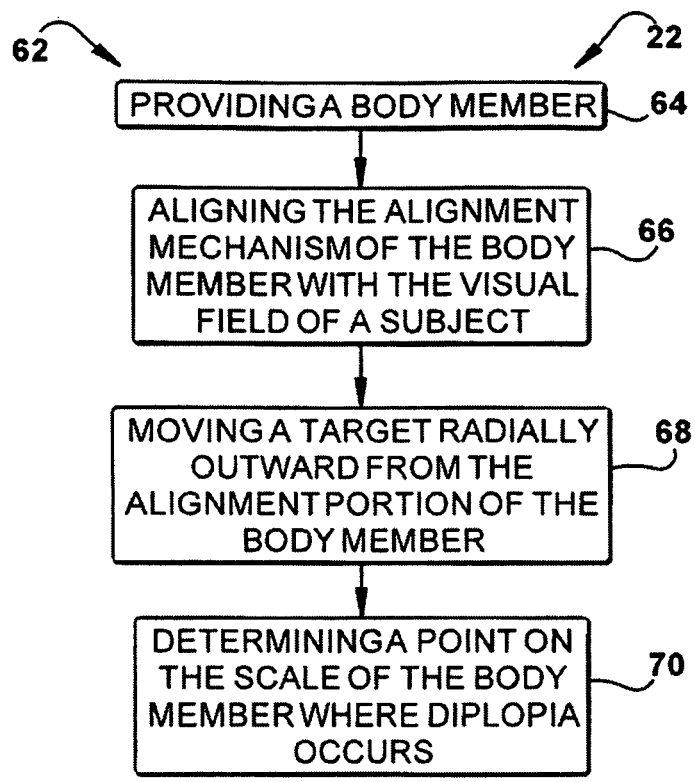
FIG. 10 is a process flowchart showing a method for assessing diplopia in a subject.

In another embodiment of the present invention, a method 62 for assessing diplopia in a subject 12 is provided (FIG. 10). As described below, the method 62 may be used to detect and quantitate the extent of diplopia in the subject 12. Further, the method 62 may be used to monitor the progression or regression of diplopia over time. The method 62 provides a simple and convenient means for automatically indexing ocular alignment that may be performed by both professional and non-professional eye care providers.

As shown in FIG. 10, the method 62 includes providing a body member 14 at 64. As shown in FIGS. 11-14, the body member 14 is constructed as shown in FIG. 1. Before use of the body member 14 begins, the body member is calibrated to determine the length $L_1$ of the arm portion 16 and the scale 32 parameters (i.e., placement of the indices 34 and their respective values).

To calibrate the body member 14, the following equation is used to convert a curved angular scale (not shown) to a linear measuring scale 32 on the arm portion 16:

$$\text{Distance of indices \textbf{34} on scale \textbf{32}} = \text{cotangent } \theta \times \text{working distance } D.$$

In the equation, the angle $\theta$ is a desired angle and, as described in more detail below, the working distance D (FIG. 11) is the distance between a point on the body member 14 (FIG. 1) and a point on the subject 12.

In one example illustrating calibration of the body member 14, a working distance D of about 16 inches may first be selected. After selecting the working distance D, at least one angle for representation on the scale 32 may be selected. Where the desired angle is about 45°, the value of $\theta$ in the calibration equation is set as 45° and the value of the working distance D is set at 16. Performing the necessary mathematical operation yields a distance value of 16 inches. Thus, as shown in FIG. 1, an indices 34 corresponding to the 45° angle is placed on the scale 32 at about 16 inches from the alignment portion 20.

In yet another example illustrating calibration of the body member 14, a working distance D of about 16 inches may first be selected. After selecting the working distance D, at least one angle for representation on the scale 32 may be selected. Where the desired angle is about 30°, the value of $\theta$ in the calibration equation is set as 30° and the value of the working distance D is set at 16. Performing the necessary mathematical operation yields a distance value of about 9 inches. Thus, as shown in FIG. 1, an indices 34 corresponding to the 30° angle is placed on the scale 32 at about 9 inches from the alignment portion 20. This calculation may then be repeated any number of times to place a number of desired indices 34 on the scale 32.

Figure 11:
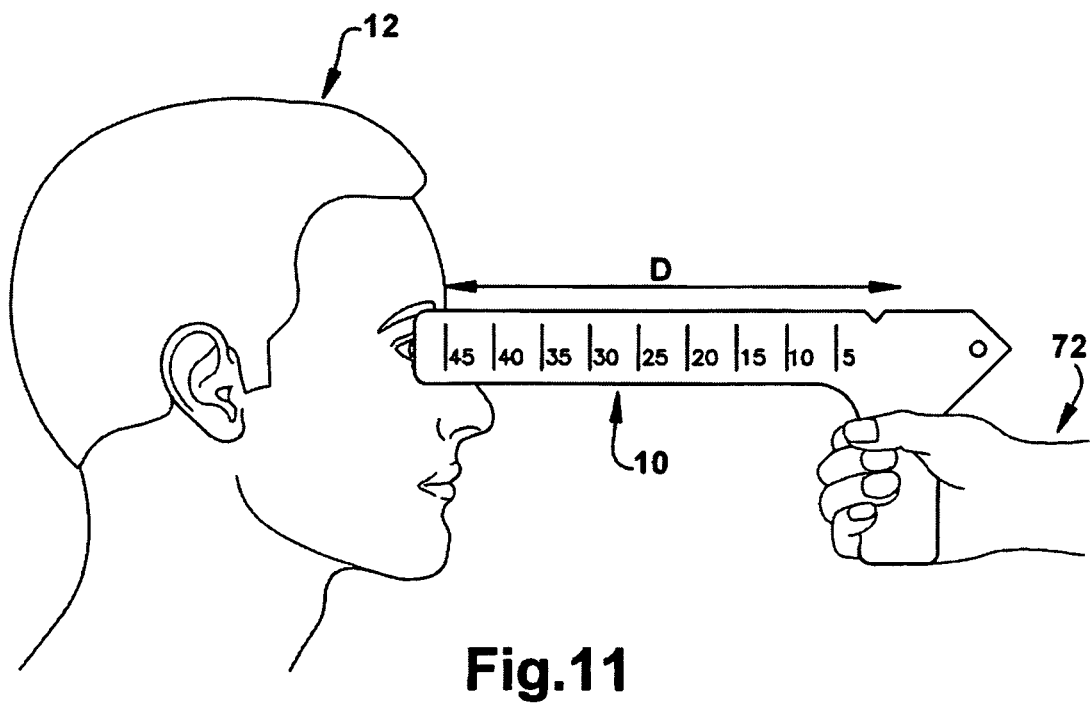
FIG. 11 is a perspective view showing a working distance between apparatus of FIG. 1 and a subject.

After the body member 14 is properly calibrated, an examiner 72 (e.g., a physician or other eye care provider) sets a working distance D between the body member and the subject 12 (FIG. 11). The working distance D is the distance between a point on the body member 14 and a point on the subject 12. As shown in FIG. 11, for example, the body member 14 is positioned such that the 45° indices 34 at the second end portion 26 of the arm portion 16 is adjacent the anterior ocular surface of the subject 12.

Figure 12A:
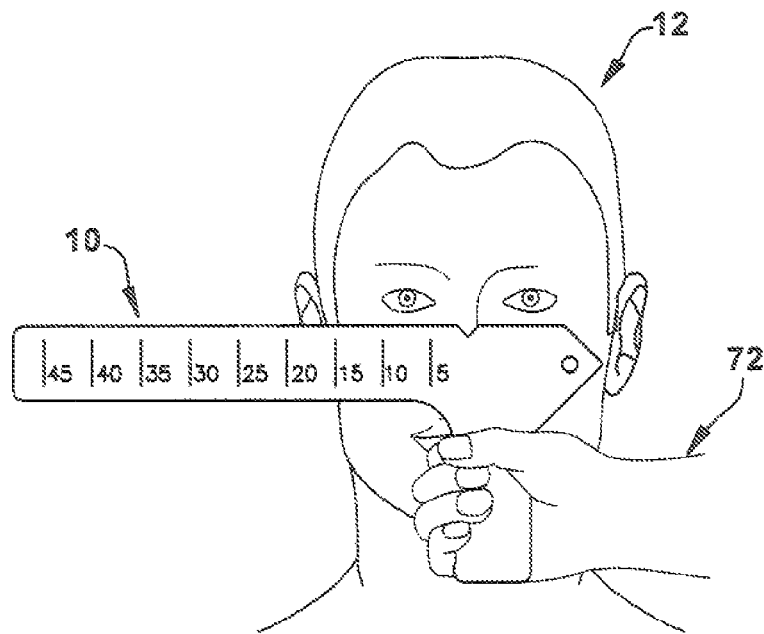
FIG. 12A is a perspective view showing the apparatus in FIG. 11 aligned with an index point on the subject.
Figure 12B:
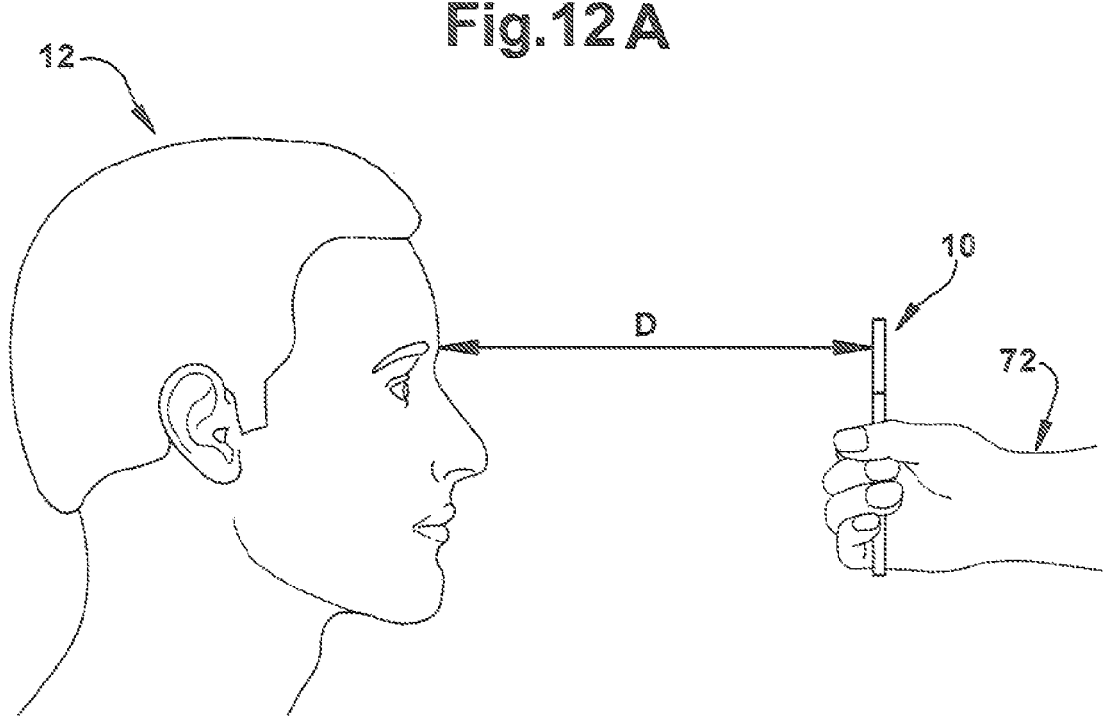
FIG. 12B is an alternative perspective view of the apparatus shown in FIG. 12A.

At 66, the alignment mechanism 40 of the body member 14 is aligned with the visual field of the subject 12. As shown in FIGS. 12A-B, the arm portion 16 of the body member 14 is rotated about 90° to a plane perpendicular to the working distance D between the examiner 72 and the subject 12. Next, the examiner 72 visually aligns an index point, i.e., the nasal bridge of the subject 12 through the indicator 42 of the alignment mechanism 40.

Figure 13:
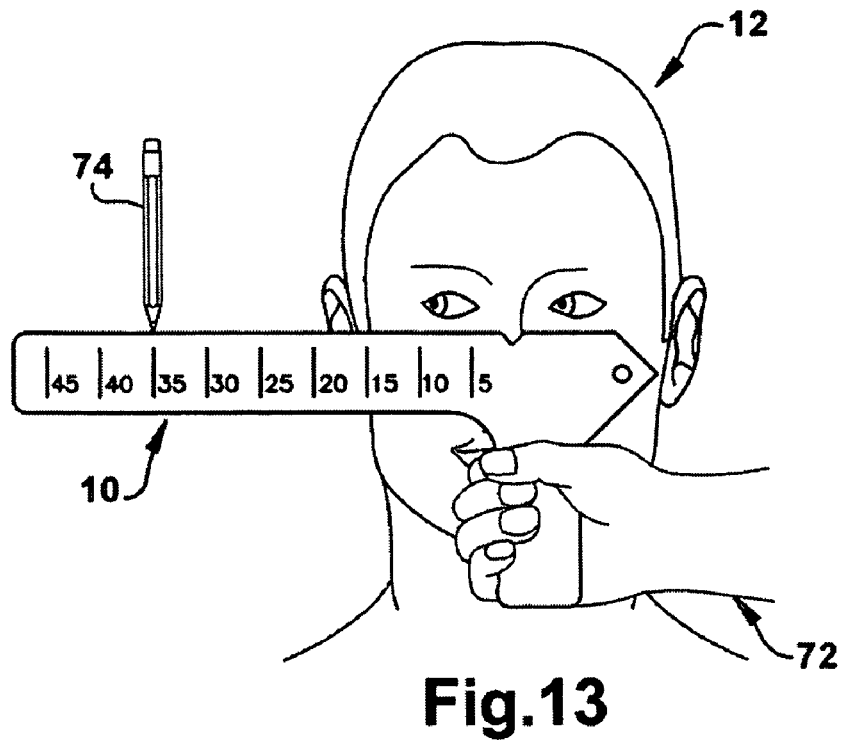
FIG. 13 is a perspective view showing a target positioned along the apparatus in FIG. 12A.
Figure 15:
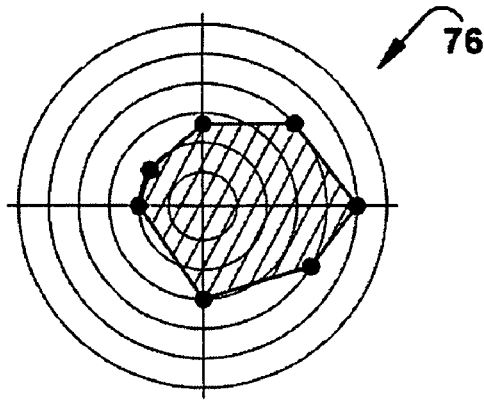
FIG. 15 is a diplopic visual field chart.

After aligning the body member 14 with the visual field of the subject 12, a target 74 (e.g., a pen) is placed at the indicator 42. At 68, the target 74 is slowly moved in a radial manner outward along the arm portion 16 (FIG. 13). The subject 12 is instructed to indicate when diplopia occurs, i.e., when the subject perceives two targets. At 70, the examiner 72 notes the position of the target 74 on the scale 32 when the subject 12 indicates the occurrence of diplopia. The examiner 72 then records the position of the target 74 (in degrees) on a diplopic visual field chart 76 (FIG. 15).

Figure 14:
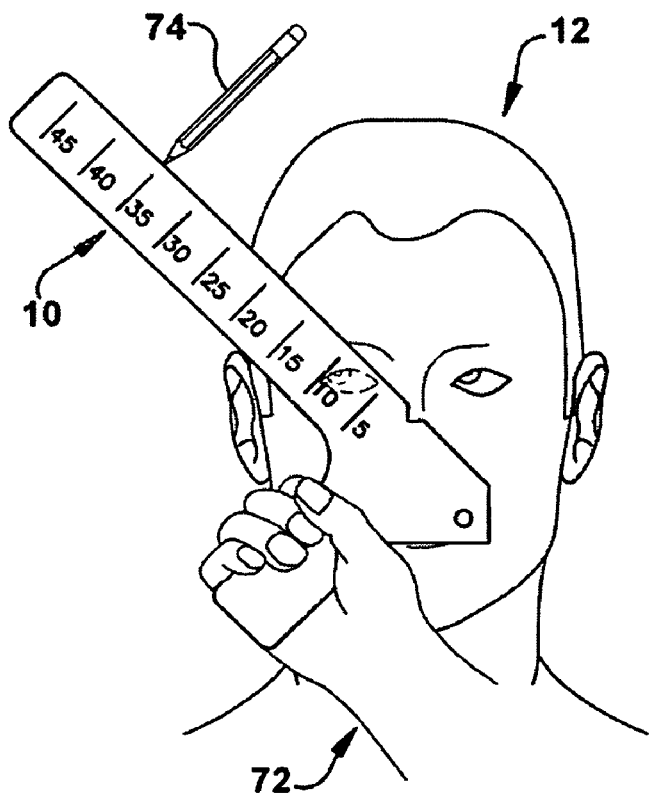
FIG. 14 is a perspective view showing the apparatus in FIG. 13 rotated to a first gaze position.

Next, the examiner 72 repositions the body member 14 so that the first angle $A_1$ is about 0° and the arm portion 16 is angled upward, i.e., the second angle $A_2$ is about 45° (FIG. 14). The target 74 is then placed at the indicator 42 and slowly moved in a radial manner outward along the arm portion 16. The subject 12 is again instructed to indicate when diplopia occurs. When the subject 12 indicates the occurrence of diplopia, the examiner 72 notes the position of the target 74 on the scale 32 and records the value on the diplopic visual field chart 76.

This process may be repeated for each of the six cardinal gaze positions, as well as the upward and downward gaze positions. For each gaze position where diplopia is reported by the subject 12, the examiner 72 notes the corresponding point on the scale 32 and records the value (in degrees) on the diplopic visual field chart 76. After the examiner 72 has tested each of the gaze positions, the diplopic visual field chart 76 is used to quantitate the field of diplopia. It should be appreciated that the information gained from the method 62 may also be used to assess extraocular muscle function. For example, where the subject 12 reports diplopia in the leftward and rightward gaze positions, a defect in the medial rectus, lateral rectus, or both may be present.

In another embodiment of the present invention, the apparatus $10_a$ shown in FIG. 2 may also be used to assess diplopia in a subject 12. Except whereas described below, the method 62 described above may be repeated to assess diplopia in the subject 12.

As described above, the body member $14_a$ may be calibrated and then aligned with the visual field of the subject 12. After aligning the alignment mechanism $40_a$ with the visual field of the subject 12, a target 74 may be placed at the indicator $42_a$. At 68, the target 74 may then be slowly moved in a radial manner outward along the arm portion $16_a$. The subject 12 may then be instructed to indicate when diplopia occurs, i.e., when the subject perceives two targets. At 70, the examiner 72 may then note the position of the target 74 on the scale 32 when the subject 12 indicates the occurrence of diplopia. The examiner 72 can then record the position of the target 74 on the scale 32, in degrees, on a diplopic visual field chart 76.

Next, the examiner 72 may rotate the arm portion $16_a$ so that the third angle $A_3$ is about 45°. The target 74 may then be placed at the indicator $42_a$ and slowly moved in a radial manner outward along the arm portion $16_a$. The subject 12 is again instructed to indicate when diplopia occurs. When the subject 12 indicates the occurrence of diplopia, the examiner 72 may then note the position of the target 74 on the scale 32 and record the value on the diplopic visual field chart 76.

This process may be repeated for each of the six cardinal gaze positions, as well as the upward and downward gaze positions. It should be appreciated, however, that any other gaze position may be assessed since the arm portion $16_a$ is adjustable to any desired third angle $A_3$. For example, the arm portion $16_a$ can be rotated such that the third angle $A_3$ is about 60°, 120°, or any variation between 0° and 360°.

After the examiner 72 has assessed a plurality of gaze positions, the diplopic visual field chart 76 may be used to quantitate the field of diplopia. It should be appreciated that the information gained from the method 62 may also be used to assess extraocular muscle function. For example, where the subject 12 reports diplopia in the leftward and rightward gaze positions, a defect in the medial rectus, lateral rectus, or both, may be present.

Figure 16:
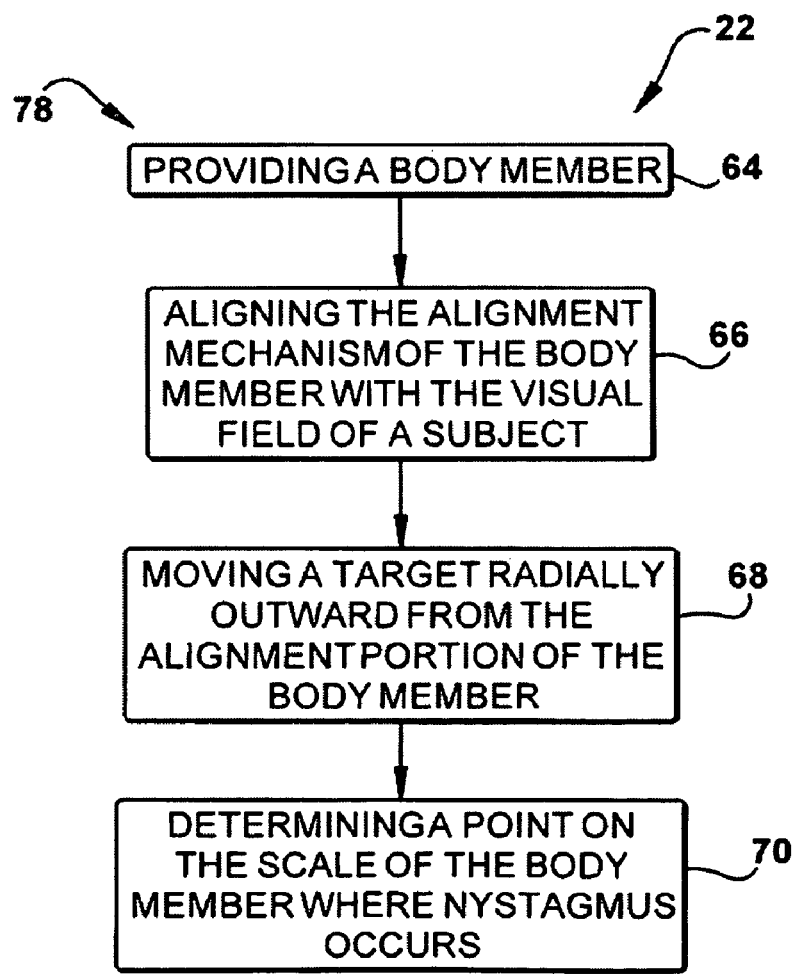
FIG. 16 is a process flowchart showing a method for assessing nystagmus in a subject.

In another embodiment of the present invention, a method 78 for assessing nystagmus in a subject 12 is illustrated in FIG. 16. The method 78 is identical to the method 62 in FIG. 10, except where as described below. In the method 78, steps that are identical to the steps in FIG. 10 use the same reference numbers, whereas steps that are similar but not identical carry the suffix "a".

As shown in FIG. 16, the method 78 includes a first step 64 of providing a body member 14. The body member 14 can comprise the body member shown in FIG. 1; however, it will be appreciated that the body member 14 may also comprise the body member $14_a$ shown in FIG. 2. Before use of the body member 14 begins, the body member may be calibrated to determine the length $L_1$ of the arm portion 16 and the parameters of the scale 32 (i.e., placement of the indices 34 on the arm portion and their corresponding values).

After the body member 14 has been properly calibrated (as described above), an examiner 72 can set a working distance D between the body member and the subject 12. The working distance D is the distance between a point on the body member 14 and a point on the subject 12. For example, the body member 14 may be positioned such that the 45° indices 34 at the second end portion 26 of the arm portion 16 is adjacent the anterior ocular surface of the subject 12.

At 66, the alignment mechanism 40 of the body member 14 may be aligned with the visual field of the subject 12. The arm portion 16 of the body member 14 may be rotated about 90° to a plane perpendicular to the working distance D. Next, the examiner 72 may visually align an index point, i.e., the nasal bridge of the subject 12 through the indicator 42 of the alignment mechanism 40.

After aligning the body member 14 with the visual field of the subject 12, a target 74 may be placed at the indicator 42. At 68, the target 74 may then be slowly moved in a radial manner outward along the arm portion 16. At $70_a$, the examiner 72 can observe the eyes of the subject 12 as the target 74 is slowly moved along the arm portion 16. When at least one eye of the subject 12 appears to twitch or appear jittery, the examiner 72 notes the position of the target 74 in degrees on the scale 32. The examiner 72 can then record the corresponding value (in degrees) on a diplopic visual field chart 76.

Next, the examiner 72 can reposition the body member 14 so that the first angle $A_1$ is about 0° and the second angle $A_2$ is about 45°. The target 74 may then be placed at the indicator 42 and slowly moved in a radial manner outward along the arm portion 16. The examiner 72 can again observe the eyes of the subject 12 and note when at least one eye appears to twitch or appear jittery. The examiner 72 can then note the position of the target 74 on the scale 32 and record the corresponding value in degrees on the diplopic visual field chart 76.

This process may be repeated for each of the six cardinal gaze positions, as well as the upward and downward gaze positions. For each gaze position where nystagmus is noted, the examiner 72 can record the corresponding value in degrees on the diplopic visual field chart 72. After the examiner 72 has tested each of the gaze positions, the visual field chart 76 may be used to quantitate the field of nystagmus. It should be appreciated that the information gained from the method 78 may also be used to assess extraocular muscle function. Where the subject 12 reports nystagmus in the leftward and rightward gaze positions, for example, a defect in the medial rectus, lateral rectus, or both may be present.

From the above description of the invention, those skilled in the art will perceive improvements, changes and modifications. For example, the present invention may additionally be used to assess the ocular range of motion in a subject 12. Such improvements, changes and modifications within the skill of the art are intended to be covered by the appended claims.

Having described the invention, the following is claimed:

1. An apparatus for assessing eye disease in a subject, said apparatus comprising:
   a body member including an arm portion, a handle portion, and an alignment portion, said arm and handle portions each having a first end portion oppositely disposed from a second end portion, each of said first end portions being operably connected to said alignment portion;
   said arm portion including a scale in degrees;
   said alignment portion including an alignment mechanism for aligning said body member with the visual field of the subject.

2. The apparatus of claim 1, wherein each of said first end portions of said arm and handle portions is fixed to said alignment portion such that said body member has a rigid, L-shaped configuration.

3. The apparatus of claim 2, wherein said alignment mechanism comprises an indicator for aligning said alignment portion with an index point on the subject and a reference surface for adjusting said body member to a desired position.

4. The apparatus of claim 1, wherein each of said first end portions of said arm and handle portions is operably attached to said alignment portion via a hinge mechanism such that said arm and handle portions are freely rotatable about a radial axis of said alignment portion.

5. The method of claim 4, wherein said alignment mechanism comprises an indicator for aligning said alignment portion with an index point on the subject and a reference wheel for adjusting said body member to a desired position.

6. A method for assessing diplopia in a subject, said method comprising the steps of:
   providing a body member comprising an arm portion, a handle portion, and an alignment portion, the arm and handle portions each having a first end portion oppositely disposed from a second end portion, each of the first end portions being operably connected to the alignment portion, the arm portion including a scale in degrees and the alignment portion including an alignment mechanism for aligning the body member with the visual field of the subject;
   aligning the alignment mechanism of the alignment portion with the visual field of the subject by rotating the body member so that the position of the arm portion corresponds to a gaze position of the subject selected from the group consisting of leftward, rightward, upward, downward, upper leftward, lower leftward, upper rightward, and lower rightward;
   moving a target radially outward from the alignment portion towards the arm portion; and
   determining the point on the scale where diplopia occurs.

7. The method of claim 6, wherein said step of providing a body member further comprises the step of calibrating the body member.

8. The method of claim 6 further comprising the step of quantitating the extent of diplopia.

9. The method of claim 8, wherein said step of quantitating the extent of diplopia includes determining a plurality of points in degrees on the scale where diplopia occurs.

10. A method for assessing nystagmus in a subject, said method comprising the steps of:
    providing a body member including an arm portion, a handle portion, and an alignment portion, the arm and handle portions each having a first end portion oppositely disposed from a second end portion, each of the first end portions being operably connected to the alignment portion, the arm portion including a scale in degrees and the alignment portion including an alignment mechanism for aligning the body member with the visual field of the subject;
    aligning the alignment mechanism of the alignment portion with the visual field of the subject by rotating the body member so that the position of the arm portion corresponds to a gaze position of the subject selected from the group consisting of leftward, rightward, upward, downward, upper leftward, lower leftward, upper rightward, and lower rightward;
    moving a target radially outward from the alignment portion towards the arm portion; and
    determining the point on the scale where nystagmus occurs.

11. The method of claim 10, wherein said step of providing a body member further comprises the step of calibrating the body member.

12. The method of claim 10 further comprising the step of quantitating the extent of nystagmus.

13. The method of claim 12, wherein said step of quantitating the extent of nystagmus includes determining a plurality of points in degrees on the scale where nystagmus occurs.

14. An apparatus for assessing eye disease in a subject, said apparatus comprising:
    a body member including an arm portion, a handle portion, and an alignment portion, said arm and handle portions each having a first end portion oppositely disposed from a second end portion, each of said first end portions being operably connected to said alignment portion such that said body member has a rigid, L-shaped configuration;
    said arm portion including a scale in degrees;
    said alignment portion including an alignment mechanism for aligning said body member with the visual field of the subject.

15. The apparatus of claim 14, wherein said alignment mechanism comprises an indicator located at said first end portion of said arm portion.

16. The apparatus of claim 14, wherein said alignment mechanism comprises a reference surface for adjusting said body member to a desired position, said reference surface having an angled, linear shape and forming a first angle with respect to a reference point.

17. The apparatus of claim 14, wherein each of said first end portions of said arm and handle portions is operably attached to said alignment portion such that said arm and handle portions are within the same plane as said alignment portion.

18. An apparatus for assessing eye disease in a subject, said apparatus comprising:
    a body member including an arm portion, a handle portion, and an alignment portion, said arm and handle portions each having a first end portion oppositely disposed from a second end portion, each of said first end portions being operably connected to said alignment portion via a hinge mechanism such that said arm and handle portions are freely rotatable about a radial axis of said alignment portion;
    said arm portion including a scale in degrees;
    said alignment portion including an alignment mechanism for aligning said body member with the visual field of the subject.

* * * * *